United States Patent [19]

Hoelderich et al.

[11] Patent Number: 4,694,107
[45] Date of Patent: Sep. 15, 1987

[54] PREPARATION OF KETONES BY ISOMERIZATION OF ALDEHYDES

[75] Inventors: Wolfgang Hoelderich; Franz Merger; Wolf D. Mross, all of Frankenthal; Rolf Fischer, Heidelberg, all of Fed. Rep. of Germany

[73] Assignee: BASF Aktiengesellschaft, Ludwigshafen, Fed. Rep. of Germany

[21] Appl. No.: 865,007

[22] Filed: Jul. 2, 1986

Related U.S. Application Data

[63] Continuation of Ser. No. 730,676, May 3, 1985, abandoned.

[30] Foreign Application Priority Data

May 24, 1984 [DE] Fed. Rep. of Germany ....... 3419378

[51] Int. Cl.$^4$ .................................... C07C 45/67
[52] U.S. Cl. .................................. 568/310; 568/341; 568/384
[58] Field of Search ................ 568/310, 388, 384, 341

[56] References Cited

U.S. PATENT DOCUMENTS

| | | | |
|---|---|---|---|
| 3,453,331 | 7/1969 | Hargis et al. | 568/388 |
| 3,466,334 | 9/1969 | Young et al. | 568/384 |
| 4,238,416 | 9/1980 | Tohzuka et al. | 568/384 |
| 4,329,506 | 5/1982 | Velenyi et al. | 568/384 |
| 4,537,995 | 8/1985 | Linstid et al. | 568/384 |

*Primary Examiner*—James H. Reamer
*Attorney, Agent, or Firm*—John H. Shurtleff

[57] ABSTRACT

Ketones are prepared by isomerization of aldehydes at elevated temperatures over zeolites.

13 Claims, No Drawings

PREPARATION OF KETONES BY ISOMERIZATION OF ALDEHYDES

This application is a continuation of application Ser. No. 730,676, filed May 3, 1985 now abandoned.

The present invention relates to a process for the preparation of ketones by isomerization of aldehydes using zeolites as catalysts.

Because of their versatility, ketones are desirable chemical compounds. They are used, for example, as solvents in the rubber and plastics industries, as solvents in chemical reactions, as extracting agents or as starting materials for organic reactions, eg. as intermediates for dyes, crop protection agents and drugs, and as fragrance materials. The preparation of ketones from aldehydes by isomerization is desirable since the aldehydes are readily obtainable, for example via the oxo synthesis. Isomerizations of this type are known. They are carried out, for example, over catalysts consisting of mixed oxides containing tin, molybdenum and copper (U.S. Pat. No. 4,329,506) or over cerium oxide on alumina (U.S. Pat. No. 3,466,334). The disadvantages of these processes are that, although the conversions are satisfactory, only low selectivities are obtained, and that the best results with respect to selectivity and catalyst life are achieved only with the addition of steam. The rapid deactivtion of the catalysts as a result of coking is also a disadvantage. Hence, in the industrial preparation of asymmetrically substituted ketones, it was as a rule necessary to rely on the condensation of various organic acids with decarboxylation, as described in German Laid-Open Application DOS No. 2,758,113. The disadvantage of this process is that symmetrically substituted ketones and carbon dioxide are inevitably produced.

We have found that, in the preparation of ketones by isomerization of aldehydes over catalysts, particularly advantageous results are obtained if the isomerization is carried out at not more than 600° C., using zeolites as catalysts.

In the novel process, high selectivities and conversions are obtained and the catalyst has a long life. Another advantage is that high selectivities are achieved without loss of catalyst activity, ie. in conjunction with a long catalyst life even in the absence of steam.

Aldehydes which can be isomerized to ketones by the novel process are, for example, those of the formula

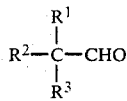   I where $R^1$ is hydrogen, methyl or ethyl, $R^2$ is hydrogen or alkyl of 1 to 10 carbon atoms and $R^3$ is alkyl of 1 to 10 carbon atoms which may furthermore contain aryl, or is aryl, cyclopentyl, cyclohexyl or a heterocyclic radical.

The alkyl radicals can be straight-chain or branched, and aryl is, for example, phenyl.

Examples of aldehydes of this type are isobutyraldehyde, 2-phenylpropanal, 2-benzylpropanal, 2-ethylhexanal, pivalaldehyde, 2-ethylbutanal, 2-methylbutanal and 2-methylpentanal. The aldehydes can be prepared by, for example, hydroformylation of olefins. Thus, 2-phenylpropanal can be obtained by hydroformylation of styrene.

Zeolites are used as catalysts for the novel isomerization of ketones to aldehydes. Zeolites are crystalline aluminosilicates which possess a highly ordered structure with a rigid three-dimensional network of $SiO_4$ and $AlO_4$ tetrahedra which are connected through common oxygen atoms. The ratio of Si and Al atoms to oxygen is 1:2. The electrovalency of the aluminum-containing tetrahedra is compensated by inclusion of cations in the crystal, eg. an alkali metal or hydrogen ion. Cation exchange is possible. The spaces between the tetrahedra are occupied by water molecules prior to dehydration by drying or calcination. The zeolites can also contain other trivalent elements such as B, Ga, Fe or Cr instead of the aluminum, and othe tetravalent elements such as Ge instead of the silicon.

Preferably used catalysts are zeolites of the pentasil type, which can have different chemical compositions, these being aluminosilicate, borosilicate, iron silicate, gallium silicate, chromium silicate, arsenosilicate and bismuth silicate zeolites or mixtures of these, and aluminogermanate, borogermanate, gallium germanate and iron germanate zeolites and mixtures of these. Aluminosilicate, borosilicate and iron silicate zeolites of the pentasil type are particularly preferred.

The aluminosilicate zeolite is prepared, for example, from an aluminum compound, preferably $Al(OH)_3$ or $Al_2(SO_4)_3$, and a silicon component, preferably highly disperse silica, in aqueous amine solution, in particular 1,6-hexanediamine, 1,3-propanediamine or triethylenetetramine solution, with or without the addition of an alkali metal or alkaline earth metal, at from 100° to 220° C., under autogenous pressure. The resulting aluminosilicate zeolites have an $SiO_2/Al_2O_3$ ratio of from 10 to 40,000, depending on the amounts of starting materials chosen. The aluminosilicate zeolites can also be prepared in an ether medium, such as diethylene glycol dimethyl ether, in an alcohol medium, such as methanol or butane-1,4-diol, or in water.

The borosilicate zeolite is synthesized, for example, at from 90° to 200° C. under autogenous pressure, by reacting a boron compound, eg. $H_3BO_3$, with a silicon compound, preferably highly disperse silica, in an aqueous amine solution, in particular 1,6-hexanediamine, 1,3-propanediamine or triethylenetetramine solution, with or without the addition of an alkali metal or alkaline earth metal. In this reaction, the aqueous amine solution may be replaced with a solution of an amine in an ether, eg. diethylene glycol dimethyl ether, or with an alcoholic solution, eg. in hexane-1,6-diol, as the solvent.

The iron silicate zeolite is obtained, for example, from an iron compound, preferably $Fe_2(SO_4)_3$, and a silicon compound, preferably highly disperse silica, in an aqueous amine solution, in particular 1,6-hexanediamine with or without the addition of an alkali metal or alkaline earth metal, at from 100° to 200° C., under autogenous pressure.

The aluminosilicate, borosilicate and iron silicate zeolites prepared in this manner are isolated, dried at from 100° to 160° C., preferably 110° C., and calcined at from 450° to 550° C., preferably 500° C., after which they can be molded with a binder in a weight ratio of from 90:10 to 40:60 to give extrudates or tablets. Suitable binders include a variety of aluminas, preferably boehmite, amorphous aluminosilicates having an $SiO_2/Al_2O_3$ ratio of from 25:75 to 95:5, preferably 75:25, silica, preferably highly disperse $SiO_2$, mixtures of highly disperse $SiO_2$ and highly disperse $Al_2O_3$, highly disperse $TiO_2$ and clay. After the molding procedure, the extrudates or tablets are dried for 16 hours at 110° C. and calcined for 16 hours at 500° C. Such catalysts can be particularly advantageously prepared by molding the isolated aluminosilicate, borosilicate or iron silicate zeolite directly after drying, the subjecting it to calcination only after the molding procedure. Fluidizable material having a particle size of from 0.1 to 0.5 mm can be obtained from the extruded catalyst by milling and screening. The aluminosilicate, borosilicate and iron silicate zeolites can, however, also be used in pure form as extrudates or tablets, without a binder. Zeolites of the mordenite type may also be used.

If, because of the method of preparation, the zeolite is not present in the acidic H form preferred for catalysis but, for example, in the Na form, it can be partially or completely converted to the desired H form by ion exchange with ammonium ions followed by calcination, or by treatment with an acid. The zeolites may furthermore be modified in a variety of ways in order to increase the selectivity, the catalyst life and the number of possible regenerations. In a suitable method of modification, for example, the unmolded or molded zeolite can be impregnated, or subjected to ion exchange, with alkali metals such as Na (provided the alkali metal form of the zeolite is not already obtained in the synthesis), with alkaline earth metals, such as Ca or Mg, or with earth metals, such as B or Tl. Doping of the zeolites with transition metals, such as Mo, W, Fe, Zn or Cu, with noble metals, such as Pd and with rare earth metals, such as Ce or La, is particularly advantageous.

In practice, such modified catalysts are produced, for example, as follows: the molded pentasil zeolite is initially taken in a siphon tube, and, for example, an aqueous solution of a halide or of a nitrate of one of the above metals is passed over at from 20° to 100° C. This type of ion exchange can be carried out, for example, over the hydrogen, ammonium or alkali metal form of the zeolite. The metal can also be applied to the zeolite by, for example, impregnating the zeolite material with a halide, a nitrate or an oxide of the above metals in an aqueous or alcoholic solution. Both ion exchange and impregnation are followed by one or more drying procedures, and, if desired, further calcination.

The specific procedure is, for example, as follows: molybdenum oxide ($moO_3$), tungstic acid ($H_2WO_4$) or $Ce(NO_3)_3.6H_2O$ is dissolved in water, or the major part of it is dissolved. This solution is then used to impregnate the extruded or unextruded zeolite for a certain time (about 30 minutes). The supernatant solution is freed from water in a rotary evaporator, after which the impregnated zeolite is dried at about 150° C. and calcined at about 550° C. This impregnation process can be carried out several times in succession in order to obtain the desired metal content.

It is also possible, for example, to prepare an ammoniacal $Pd(NO_3)_2$ solution, and to suspend the pure zeolite powder therein for about 24 hours at from 40° to 100° C., while stirring. After filtration, drying at about 150° C. and calcination at about 500° C., the zeolite material thus obtained can be further processed, with or without a binder, to give extrudates, pellets or fluidizable material.

Ion exchange with the zeolite in the H form can be carried out by initially introducing the zeolite in the form of extrudates or pellets into a column, and circulating over it, for example, an ammoniacal $Pd(NO_3)_2$ solution at slightly elevated temperatures of from 30° to 80° C. for from 15 to 20 hours. This is followed by washing thoroughly with water, drying at about 150° C. and calcining at about 550° C.

For some metal-doped zeolites, after-treatment with hydrogen is advantageous.

In another possible method of modification, the zeolite material, in molded or unmolded form, is subjected to a treatment with an acid, such as hydrochloric acid, hydrofluoric acid or phosphoric acid and/or with steam. In an advantageous procedure, for example, the zeolite powder, before being molded, is treated with from 0.001 to 2N, preferably from 0.05 to 0.5N, hydrofluoric acid under reflux for from 1 to 3 hours. The product is filtered off and washed thoroughly, after which it is dried at from 100° to 160° C. and calcined at from 400° to 550° C. It may also be advantageous to treat the zeolites with hydrochloric acid after they have been molded with the binder. In this procedure, the zeolite is treated with, for example, from 3 to 25, in particular from 12 to 20, % strength hydrochloric acid at from 60° to 80° C. for from 1 to 3 hours, and then washed thoroughly, dried at from 100° to 160° C. and calcined at from 400° to 550° C. The zeolite may also be modified by applying phosphorus compounds, such as trimethoxyphosphate.

When the zeolite catalysts have become deactivated, which may occur as a result of coking during the process of the invention, they can be regenerated in a simple manner by burning off the coke deposit with air or with an air/$N_2$ mixture at from 400° to 550° C., preferably 500° C., with the result that they again attain their initial activity. The activity of the catalyst can furthermore be set to achieve optimum selectivity of the desired product by partial coking (pre-coke). If the isomerization is carried out in the presence of gases such as hydrogen, nitrogen and steam, the product composition and the life of the catalyst can be influenced by these. In general, the catalysts are used alternatively as 2–4 mm extrudates, as tablets having a diameter of from 3 to 5 mm, or as a powder having particle sizes of from 0.3 to 0.5 mm or (as a fluidizable catalyst) from 0.1 to 0.5 mm.

The isomerization of the aldehydes to the ketones is carried out over the zeolites preferably in the gas phase at from 100° to 600° C., in particular from 250° to 500° C. The space velocity (WHSV) is from 0.1 to 20, preferably from 0.5 to 5, g of aldehyde per g of catalyst per hour. The isomerization may also be carried out in the liquid phase, for example at from 30° to 300° C. The process can be effected by a batchwise or continuous method, under atmospheric or superatmospheric pressure, for example in a continuous-flow reactor, a stirred kettle or a fluidized-bed reactor. Unconverted aldehydes can, if required, be separated off from the resulting ketones by distillation after reaction, and can be reused for the reaction according to the invention.

EXAMPLE 1

To isomerize it to phenylacetone, 2-phenylpropanal was introduced into a tube reactor (spiral form, internal diameter 0.6 cm, (length 90 cm) under isothermal conditions, and passed over a zeolite catalyst at 400° C., in the gas phase. The reaction products obtained were worked up by distillation and characterized by their boiling points, refractive indices and NMR spectra. Quantitative determination of the products and of the starting materials was carried out by gas chromatography. The type of catalyst, the space velocity (WHSV), the conversion and the selectivity are shown in Table I below.

at 500° C. The process was repeated several times until the Na content of the catalyst had fallen below 0.03% by weight.

TABLE I

| Catalyst | A | B | C | D | E | F | G | H | I | J |
|---|---|---|---|---|---|---|---|---|---|---|
| Temperature °C. | 400 | 400 | 350 | 400 | 400 | 400 | 400 | 400 | 400 | 400 |
| WHSV | 0.8 h$^{-1}$ | 2.4 h$^{-1}$ | 3.1 h$^{-1}$ | 2 h$^{-1}$ | 2.4 h$^{-1}$ | 2.4 h$^{-1}$ | 2.4 h$^{-1}$ | 2 h$^{-1}$ | 2.4 h$^{-1}$ | 2.4 h$^{-1}$ |
| Product composition % by weight | | | | | | | | | | |
| Aldehyde | 37.0 | 53.6 | 32.9 | — | 21.9 | 46.2 | 20.0 | 16.1 | 33.2 | 8.5 |
| Ketone | 61.3 | 42.3 | 64.5 | 86.6 | 73.0 | 49.8 | 77.1 | 77.3 | 56.3 | 78.2 |
| Conversion % | 63.0 | 46.4 | 67.1 | 100 | 79.1 | 53.8 | 80.0 | 83.9 | 66.8 | 91.5 |
| Selectivity of ketone % | 97.3 | 91.2 | 96.1 | 86.6 | 92.3 | 92.6 | 96.4 | 92.1 | 84.3 | 85.5 |

The catalysts used were prepared as described below:

Catalyst A

The catalyst was prepared by a hydrothermal synthesis from 64 g of $SiO_2$ (highly disperse silica), 12.2 g of $H_3BO_3$ and 800 g of aqueous hexanediamine solution (50:50 (w/w) mixture) at 170° C. under autogenous pressure in a stirred autoclave. The crystalline product was filtered off, washed thoroughly, dried at 100° C. for 24 hours and calcined at 500° C. for 24 hours. The product obtained was a borosilicate zeolite of the pentasil type which contained 92.4% by weight of $SiO_2$ and 2.32% by weight of $B_2O_3$. This zeolite was converted to 2 mm extrudates, which were dried at 100° C. and calcined for 24 hours at 500° C.

Catalyst B

An aluminosilicate zeolite of the pentasil type was prepared under hydrothermal conditions, under autogenous pressure and at 150° C., from 65 g of highly disperse $SiO_2$ and 20.3 g of $Al_2(SO_4)_3.18H_2O$ in 1 kg of an aqueous 1,6-hexanediamine solution (50:50 (w/w) mixture) in a stirred autoclave. The crystalline product was filtered off, washed thoroughly, dried at 110° C. for 24 hours and calcined at 500° C. for 24 hours. This aluminosilicate zeolite contained 91.6% by weight of $SiO_2$ and 4.6% by weight of $Al_2O_3$. The catalyst was molded to give 2 mm extrudates, and the latter were dried at 110° C. for 16 hours and calcined at 500° C. for 24 hours.

Catalyst C

The iron silicate zeolite of the pentasil type was synthesized under hydrothermal conditions, under autogenous pressure and at 165° C., from 273 g of waterglass, dissolved in 253 g of an aqueous 1,6-hexanediamine solution (50:50 (w/w) mixture), and 31 g of iron sulfate, dissolved in 21 g of 96% strength sulfuric acid and 425 g of water, in a stirred autoclave in the course of 4 days. The zeolite was filtered off, washed thoroughly, dried at 100° C. for 24 hours and calcined at 500° C. for 24 hours. The iron silicate zeolite obtained had an $SiO_2$/$Fe_2O_3$ ratio of 17.7 and an $Na_2O$ content of 1.2% by weight. The catalyst was converted to 2.5 mm extrudates, which were dried at 110° C. for 16 hours and calcined at 500° C. for 24 hours.

Catalyst D

This catalyst was prepared from an iron silicate zeolite as described under catalyst C, by conversion to extrudates with boehmite in a weight ratio of 60:40, followed by calcination at 500° C. for 16 hours. The extrudates were subjected to ion exchange with a 20% strength aqueous $NH_4Cl$ solution at 80° C. and calcined

Catalyst E

The catalyst was prepared in the same manner as catalyst B, except that the 1,6-hexanediamine was replaced with 1,3-propanediamine. The aluminosilicate zeolite obtained contained 90.6% by weight of $SiO_2$ and 3.4% by weight of $Al_2O_3$.

Catalyst F

The catalyst was prepared from the aluminosilicate zeolite whose synthesis is described under catalyst B. The zeolite powder was extruded, in a weight ratio of 60:40, with highly disperse $SiO_2$ containing from 0.3 to 1.3% by weight of highly disperse $Al_2O_3$, 2 mm extrudates being produced. The extrudates were dried at 110° C. for 16 hours and calcined at 500° C. for 16 hours.

Catalyst G

To prepare the catalyst, the borosilicate zeolite obtained as described under A was treated with HF. In this procedure, 50 g of the borosilicate zeolite were refluxed with 140 ml of 0.1N HF for 1 hour, and the product was filtered off, washed neutral with water, dried at 110° C. for 16 hours and calcined at 500° C. for 5 hours. This material was pressed to 5 mm tablets.

Catalyst H

The catalyst was prepared from catalyst G by molding, in a weight ratio of 60:40, with highly disperse $SiO_2$ containing from 0.3 to 1.3% by weight of highly disperse $Al_2O_3$, to give 2 mm extrudates.

Catalyst I

Catalyst A was converted to 2 mm extrudates with boehmite in a weight ratio of 60:40. The extrudates were dried at 110° C. for 16 hours, calcined at 500° C. for 16 hours and then impregnated with an aqueous solution of $Cu(NO_3)_2.3H_2O$ for 30 minutes. The residual water was extracted under reduced pressure in a rotary evaporator, and the extrudates were dried and calcined. The Cu content was 3.5% by weight.

Catalyst J

The procedure described under catalyst I was followed, except that the $Cu(NO_3)_2.3H_2O$ was replaced with $MoO_3$. Where necessary, the impregnation process had to be repeated until the extrudates had an Mo content of 1.1% by weight.

EXAMPLE 2

To determine the effect of the temperature on the conversion and the selectivity, Example 1 was repeated using catalyst A at 250° C. and 500° C. The results are shown in Table II.

TABLE II

| Catalyst | A | A | A |
|---|---|---|---|
| Temperature °C. | 250 | 400 | 500 |
| WHSV | 0.8 h$^{-1}$ | 0.8 h$^{-1}$ | 0.8 h$^{-1}$ |
| Product composition % by weight | | | |
| Aldehyde | 84.5 | 37.0 | 12.0 |
| Ketone | 15.4 | 61.3 | 79.9 |
| Conversion % | 15.5 | 63.0 | 88.0 |
| Selectivity ketone % | 99.3 | 97.3 | 90.8 |

EXAMPLE 3

In order to isomerize it to methyl ethyl ketone, isobutyraldehyde was reacted by the procedure described in Example 1. The results are shown in Table III.

TABLE III

| Catalyst | A | A |
|---|---|---|
| Temperature °C. | 400 | 500 |
| WHSV | 2 h$^{-1}$ | 2 h$^{-1}$ |
| Conversion % | 41.9 | 96.8 |
| Selectivity of ketone % | 89.5 | 62.5 |

EXAMPLE 4

In order to isomerize it to methyl isopropyl ketone, pivalaldehyde was reacted by the procedure described in Example 1. The results are shown in Table IV.

TABLE IV

| Catalyst | A | A |
|---|---|---|
| Temperature °C. | 250 | 350 |
| WHSV | 2 h$^{-1}$ | 2 h$^{-1}$ |
| Conversion % | 13.2 | 92.4 |
| Selectivity of ketone % | 80.1 | 84.5 |

We claim:

1. In a process for the preparation of a ketone by isomerization of an aldehyde in the presence of a zeolite catalyst, the improvement which comprises:

converting into said ketone an aldehyde of the formula

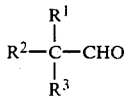

$$R^2-\underset{\underset{R^3}{|}}{\overset{\overset{R^1}{|}}{C}}-CHO \qquad I$$

where $R^1$ is hydrogen, methyl or ethyl, $R^2$ is hydrogen or alkyl of 1 to 10 carbon atoms and $R^3$ is alkyl of 1 to 10 carbon atoms or said alkyl which is substituted by an aryl radical, or further where $R^3$ is an aryl, cyclopentyl, cyclohexyl or heterocyclic radical, at not more than 600° C. over a zeolite catalyst which is selected from the group consisting of a borosilicate zeolite of the pentasil type and an iron silicate zeolite of the pentasil type.

2. A process as claimed in claim 1, wherein 2-phenylpropanal is isomerized to phenylacetone.

3. A process as claimed in claim 1, wherein isobutyraldehyde is isomerized to methyl ethyl ketone.

4. A process as claimed in claim 1, wherein pivalaldehyde is isomerized to methyl isopropyl ketone.

5. A process as claimed in claim 1, wherein a borosilicate zeolite of the pentasil type is used.

6. A process as claimed in claim 1, wherein an iron silicate zeolite of the pentasil type is used.

7. A process as claimed in claim 1, wherein the conversion of the aldehyde over the zeolite is carried out in the gas phase at from 250° to 500° C.

8. In a process for the preparation of a ketone by isomerization of an aldehyde in the presence of a zeolite catalyst, the improvement which comprises:

converting into said ketone an aldehyde of the formula

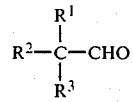

$$R^2-\underset{\underset{R^3}{|}}{\overset{\overset{R^1}{|}}{C}}-CHO \qquad I$$

where $R^1$ is hydrogen, methyl or ethyl, $R^2$ is hydrogen or alkyl of 1 to 10 carbon atoms and $R^3$ is alkyl of 1 to 10 carbon atoms or said alkyl which is substituted by an aryl radical, or further where $R^3$ is an aryl, cyclopentyl, cyclohexyl or heterocyclic radical, at not more than 600° C. over a zeolite catalyst which is an aluminosilicate zeolite of the pentasil type as obtained by the steps which include heating an aluminum compound and a silicon component in an aqueous solution of an amine at from 100° to 220° C.

9. A process as claimed in claim 8 wherein the aluminum compound of the zeolite catalyst is selected from the group consisting of Al(OH)$_3$ and Al$_2$(SO$_4$)$_3$.

10. A process as claimed in claim 8 wherein the silica component of the zeolite catalyst is a highly dispersed silica.

11. A process as claimed in claim 8 wherein the amine used in said aqueous solution is selected from the group consisting of 1,6-hexanediamine, 1,3-propanediamine and triethylenetetraamine.

12. A process as claimed in claim 8 wherein the zeolite has an SiO$_2$/Al$_2$O$_3$ ratio of from 10 to 40,000.

13. A process as claimed in claim 8 wherein the aldehyde is selected from the group consisting of 2-phenylpropanal, isobutyraldehyde and pivalaldehyde for conversion to phenylacetone, methyl ethyl ketone and methyl isopropyl ketone, respectively.

* * * * *